US00PP17284P2

(12) United States Plant Patent
Greiner

(10) Patent No.: US PP17,284 P2
(45) Date of Patent: Dec. 19, 2006

(54) APPLE TREE NAMED 'GRE-1198'

(50) Latin Name: *Malus Mill.*
Varietal Denomination: GRE-1198

(76) Inventor: Mark Greiner, 119 Lattintown Rd., Newburg, NY (US) 12550

( * ) Notice: Subject to any disclaimer, the term of this patent is extended or adjusted under 35 U.S.C. 154(b) by 0 days.

(21) Appl. No.: 11/084,371

(22) Filed: Mar. 17, 2005

Related U.S. Application Data

(60) Provisional application No. 60/554,744, filed on Mar. 18, 2004.

(51) Int. Cl.
*A01H 5/00* (2006.01)

(52) U.S. Cl. ..... Plt./172

(58) Field of Classification Search ..... Plt./172
See application file for complete search history.

*Primary Examiner*—Anne Marie Grunberg
*Assistant Examiner*—Annette H Para
(74) *Attorney, Agent, or Firm*—Stratton Ballew PLLC

(57) ABSTRACT

A new and distinct apple tree named 'GRE-1198' is disclosed. The fruit of 'GRE-1198' is notable for its large size, crunchy texture and sweet taste as compared to other golden-type apples.

3 Drawing Sheets

Latin name of the genus and species of the plant claimed: *Malus Mill.*
Variety denomination: 'GRE-1198'.

BRIEF DESCRIPTION OF THE PHOTOGRAPHS

BACKGROUND AND SUMMARY OF THE NEW VARIETY

Figure 1:
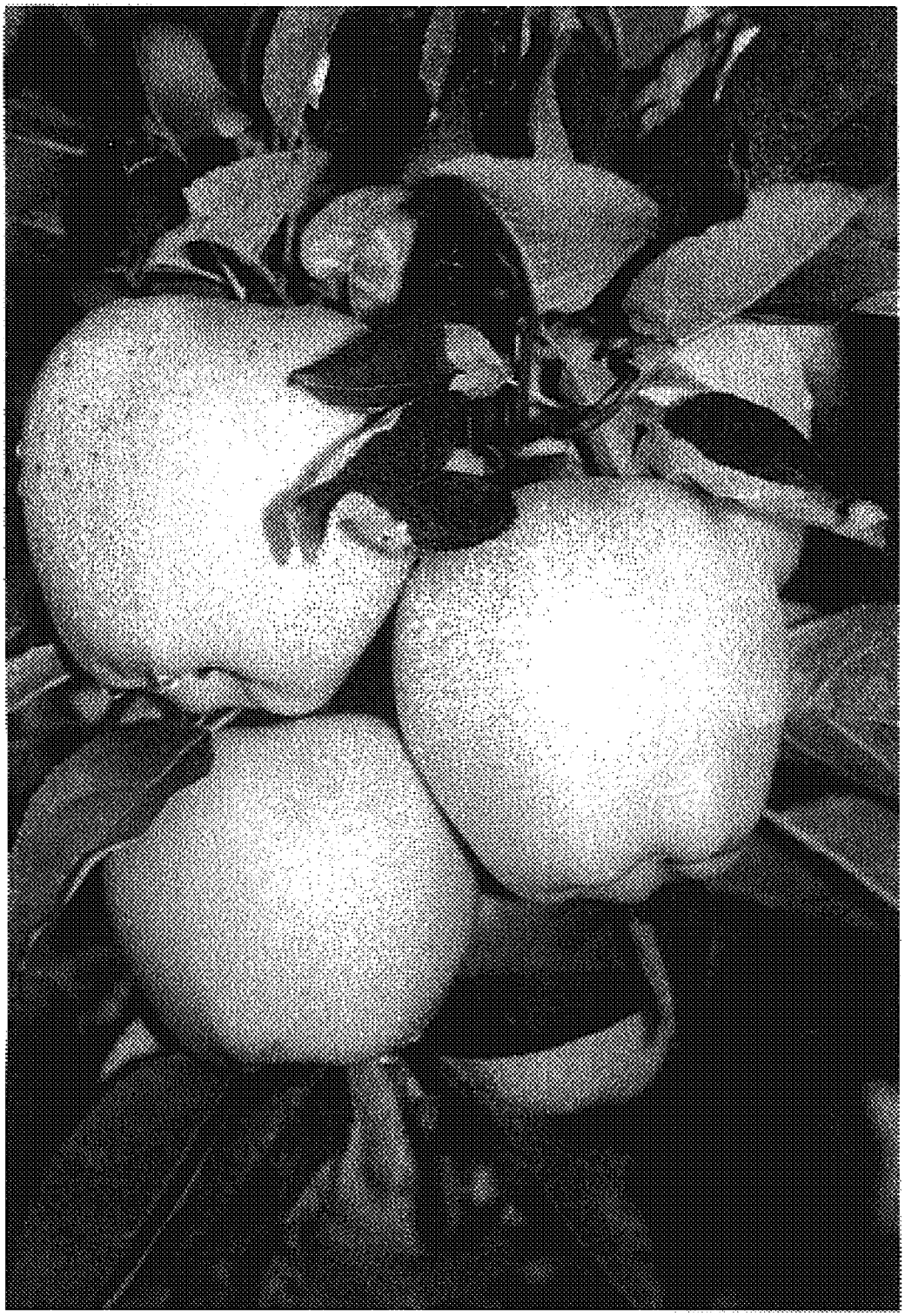
FIG. 1 shows the fruit and leaves of 'GRE-1198'.
Figure 2:
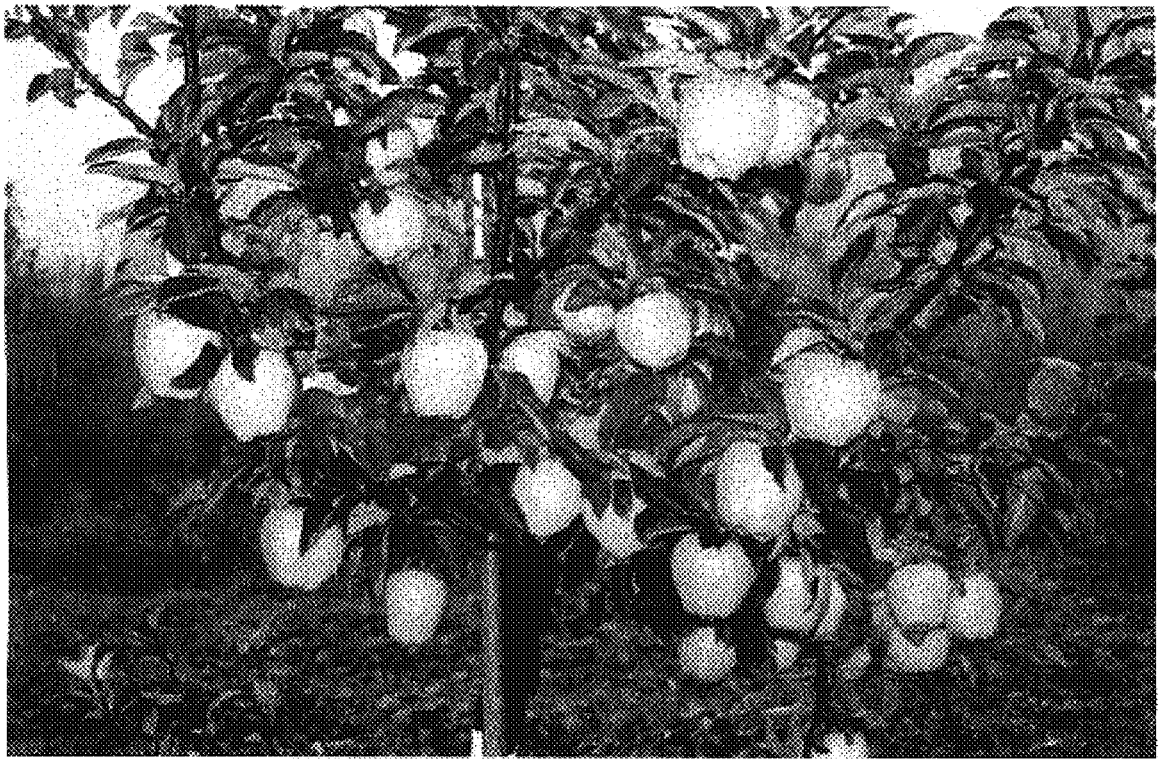
FIG. 2 shows the fruit, leaves and branches of 'GRE-1198'.
Figure 3:
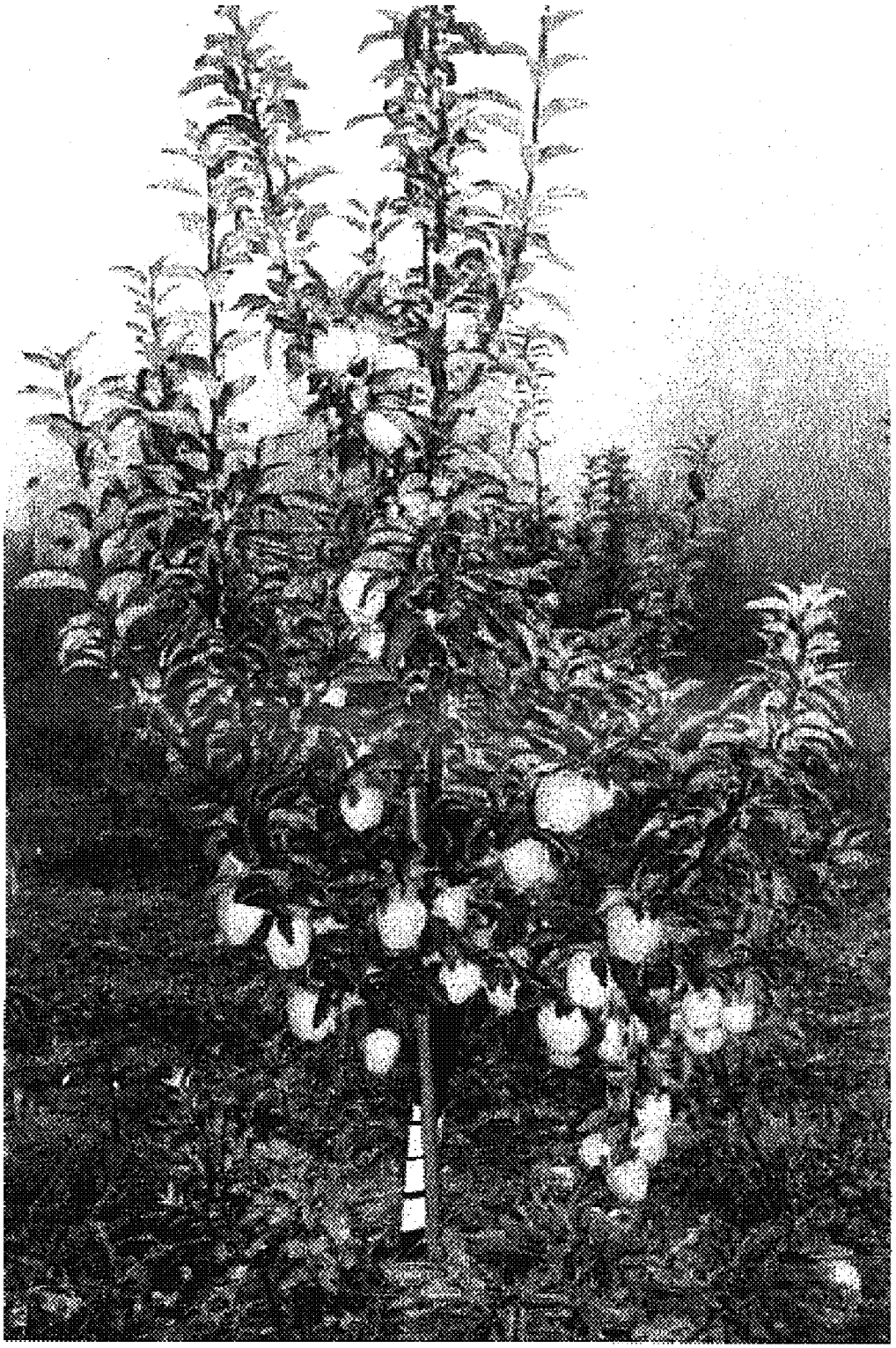
FIG. 3 shows a tree of 'GRE-1198'.

'GRE-1198' is a new and distinct golden-type apple tree. It was discovered by the inventor as a chance seedling of unknown parentage in a cultivated orchard near Marlboro, N.Y., and was found to be unlike other, known varieties. Scion wood of the parent tree was topworked onto existing trees, and second generation fruit was obtained. Further asexual propagation conducted at Marlboro, N.Y. has shown the cultivar to remain true to type through successive asexual propagations. The fruit of 'GRE-1198' is notable for its large size, crunchy texture and sweet, pear-like taste as compared to other golden-type apples. 'GRE-1198' is further distinguishable from other golden-type apple trees by its late maturing fruit and tendency toward heavy bearing on upright limbs. Fruit of 'GRE-1198' does well in storage, without the tendency to wrinkle that is common in other golden-type apples.

DETAILED BOTANICAL DESCRIPTION

The following is a botanical description of 'GRE-1198', based on observations of four year old specimens grown near Marlboro, N.Y., USA during the 2003 and 2004 growing seasons. All colors are described according to The Royal Horticultural Society Colour Chart. It should be understood that the botanical features described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Extremely vigorous; upright habit; heavy bearer; height 335 cm; spread 396 cm; trunk diameter 7.6 cm at 10 cm above ground; trunk color grey 201A, smooth; trunk lenticels predominantly round or elliptical, diameter 5 mm.

Branches: Scaffold branch diameter 34.3 mm at 1.0 cm from main trunk; crotch angle 59°; branch lenticels predominantly round or elliptical, diameter 1.2 mm.

Leaf: Length 65 mm, width 46 mm; margin serrulate; ovate with acuminate tip, aequilateral base; color yellow-green 147A; medium pubescence, fine on young leaves; petiole length 35 mm.

Flower: Diameter 40 mm; petals ovoid to round, length 17 mm, width 10 mm; color violet 84D to white N155A, with coloring blending in sharply at tip of petal; stamen length 7 to 9 mm; pistil length 7 to 9 mm, style fused at base, color yellow green 150D; flowers at same time as 'Golden Delicious' (unpatented).

Fruit (eating ripe):

*Size.*—Large, 89 mm diameter; 292 g.

*Color.*—Ranges from yellow green 151A to yellow 11B as fruit matures; may have areas of blush greyed-orange 163B.

*Shape.*—Globose conical; prominent calyx lobes, slightly ribbed.

*Bloom of skin.*—Absent or very weak.

*Lenticels.*—Conspicuous, greyed-orange 173C and greyed-green 197C.

*Russetting.*—Not prone, only slight russet in stem cavity, color greyed-green 197C.

*Flesh.*—Firm, crisp, very juicy; distinctive pear flavor, very sweet and mild as compared to other golden type apples; color yellowish cream 11D; 17 to 18° Brix.

*Core.*—Width 10 mm, length 22 mm, core lines irregular.

*Seed.*—0 to 2 seeds per cell; length 3 mm, width 1.5 mm, color greyed-orange 166A.

*Pedicel.*—Length 1.1 cm, thick, slight club on end; slightly pubescent; color greyed-green 197B; very firmly attached, tendency to break rather than release when pulled.

*Eye.*—Sepals connivent, upright with joints meeting and overlapping; basin diameter 3.7 cm.

*Time of maturity for consumption.*—Very late (late October to early November in Marlboro, N.Y., USA); matures with 'Fuji' (unpatented) or late 'Rome' (unpatented).

Market use: Culinary, dessert.

It is claimed:

1. What is claimed is a new and distinct apple tree substantially as shown and described herein.

* * * * *